United States Patent [19]

Stavinoha et al.

[11] Patent Number: 5,026,886
[45] Date of Patent: Jun. 25, 1991

[54] PREPARATION OF BIDENTATE LIGANDS

[75] Inventors: Jerome L. Stavinoha; Gerald W. Phillips; Thomas A. Puckette; Thomas J. Devon, all of Longview, Tex.

[73] Assignee: Eastman Kodak Company, Rochester, N.Y.

[21] Appl. No.: 148,241

[22] Filed: Jan. 25, 1988

[51] Int. Cl.$^5$ .............. C07F 9/66; C07F 9/92; C07F 9/94; C07F 9/50

[52] U.S. Cl. .............. 556/70; 556/71; 556/87; 556/88; 568/8; 568/17; 558/303; 562/405; 562/606; 560/103; 560/231; 564/15

[58] Field of Search .............. 568/8, 17; 556/70, 71, 556/87, 88; 558/303; 560/103, 234; 562/405, 606; 564/15

[56] References Cited

U.S. PATENT DOCUMENTS

| | | | |
|---|---|---|---|
| 3,048,638 | 8/1962 | Foster | 568/8 |
| 3,239,566 | 3/1966 | Slaugh et al. | 260/604 |
| 3,527,809 | 9/1970 | Pruett et al. | 260/604 |
| 3,539,622 | 11/1970 | Heck | 260/515 |
| 3,636,168 | 1/1972 | Josephson | 260/645 |
| 3,748,350 | 7/1973 | Josephson | 260/475 |
| 4,105,705 | 8/1978 | Lareck | 260/668 |
| 4,138,420 | 2/1979 | Unruh et al. | 260/439 |
| 4,139,565 | 2/1979 | Unruh et al. | 260/604 |
| 4,152,344 | 5/1979 | Unruh | 260/439 |
| 4,169,861 | 10/1979 | Hughes | 260/604 |
| 4,193,943 | 3/1980 | Unruh et al. | 260/604 |
| 4,201,728 | 5/1980 | Hughes | 568/454 |
| 4,212,831 | 7/1980 | Nakayama et al. | 568/17 |
| 4,221,744 | 9/1980 | Unruh | 568/454 |
| 4,229,381 | 10/1980 | Ogata et al. | 568/454 |
| 4,263,466 | 4/1981 | Colon et al. | 585/421 |
| 4,326,989 | 4/1982 | Colon et al. | 252/429 |
| 4,556,740 | 12/1985 | Hansen et al. | 568/17 |

FOREIGN PATENT DOCUMENTS

| | | | |
|---|---|---|---|
| 4639337 | 8/1968 | Japan | 568/17 |
| 56-99494 | 1/1980 | Japan | 568/17 |

OTHER PUBLICATIONS

Wittenberg & Gilman, Journal of Organic Chemistry, vol. 23, pp. 1063-1065, (1958).
Bailey & Erickson, Organic Synthesis, vol. 41, pp. 41-45 (1961).
Bailey & Erickson, Organic Synthesis, vol. 41, pp. 46-48 (1961).
Rieke & Bales, Journal of the American Chemical Society, vol. 96, pp. 1775-1781 (1974).
Kende, Liebeskind & Braitsch, Tetrahedron Letters, pp. 3375-3378 (1975).
Tamao, et al., Bulletin of the Chemical Society of Japan, vol. 49, pp. 1958-1969 (1976).
Zembayashi, Tamao, Yoshida & Kumada, Tetrahedron Letters, pp. 4089-4092 (1977).
Colon & Kelsey, Journal of Organic Chemistry, vol. 51, pp. 2627-2637 (1986).
Bishop et al., J. Organometal. Chem., 27 (1971), 241-249.
Bornsov et al., Izvest. Akad. Nauk SSSR, No. 7, 1258-1261 (1962).
Kosolapoff and Maier, *Organic Phosphorus Compounds*, New York; Wiley-Interscience, 1972.
Kemp and Vallaccio, *Organic Chemistry*, New York; Worth Publishers, Inc., 1980.

*Primary Examiner*—Paul F. Shaver
*Attorney, Agent, or Firm*—J. Frederick Thomsen; William P. Heath, Jr.; S. E. Reiter

[57] ABSTRACT

A process is disclosed for preparing biaryl, bidentate ligands comprising:

(1) contacting a biaryl compound having the structural formula:

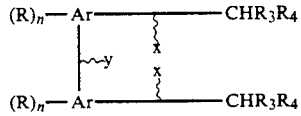

with a proton abstracting agent under conditions suitable to form a biaryl dianion, which is then (2) contacted with a Group V compound of the formula:

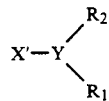

where X' is halogen or a suitable leaving group.

26 Claims, No Drawings

PREPARATION OF BIDENTATE LIGANDS

DESCRIPTION

This invention relates to the preparation of bidentate ligands which are useful, for example, in the formation of low pressure hydroformylation catalysts.

BACKGROUND OF THE INVENTION

Bidentate ligands have recently been shown to be very effective for the preparation of organometallic catalysts, such as for example, low pressure hydroformylation catalysts wherein the bidentate ligands are coordinated with rhodium. While a variety of bidentate ligands are useful for such chemical conversions as hydroformylation, their synthesis is often difficult, involving numerous reaction steps, one or more of which give low product yields. The net result is that the target bidentate ligands are obtained in low overall yields and are expensive to prepare.

In order for bidentate ligands such as:

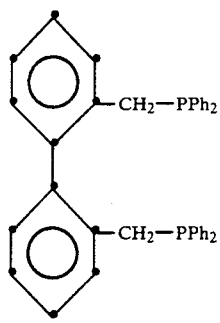

to come into more widespread use, efficient means for the preparation of such bidentate ligands will need to be developed.

OBJECTS OF THE INVENTION

It is, therefore, an object of the present invention to develop improved methods for the preparation of bis(-dihydrocarbylphosphinomethyl)biphenyl-type bidentate ligands.

This and other objects will become apparent from inspection of the detailed description and claims which follow.

STATEMENT OF THE INVENTION

In accordance with the present invention, we have discovered that bis(dihydrocarbylphosphinomethyl)-biphenyl-type compounds can be prepared from a bis-(alkyl substituted) biaryl compound by a simple two-step procedure, which involves first, the deprotonation of the bis(alkyl substituted) biaryl compound, which is then converted to the desired bidentate ligand by reaction of the biaryl dianion with Group V compounds of specified structure (e.g., chlorodiphenylphosphine).

The resulting diphosphine compounds are useful as bidentate ligands in combination with a wide variety of active metal species. For example, when employed in combination with rhodium, the bis(dihydrocarbylphosphinomethyl)biphenyl-type compounds prepared in accordance with the present invention are useful as components of low pressure hydroformylation processes. Such catalyst systems produce unusually high proportions of normal (or unbranched) aldehydes from $\alpha$-olefins, e.g., n-butyraldehyde from propylene.

DETAILED DESCRIPTION OF THE INVENTION

In accordance with the present invention, there is provided a process for preparing a bidentate ligand of the formula:

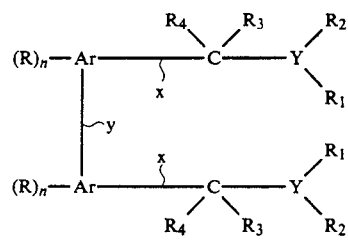

wherein:

each Ar is independently selected from aromatic ring compounds having 6 up to 14 carbon atoms, e.g., phenyl, naphthyl, phenanthryl and anthracenyl;

the x bonds and the y bonds are attached to adjacent carbon atoms on the ring structures;

each R, when present as a substituent, is independently selected from alkyl, alkoxy, aryloxy, aryl, aralkyl, alkaryl, alkoxyalkyl, aryloxyalkyl, cycloaliphatic, halogen, alkanoyl, aroyl, alkanoyloxy, aroyloxy, alkoxycarbonyl, aryloxy carbonyl, carboxyl, cyano, sulfonic acid or formyl radicals;

n is a whole number in the range of 0–4 where Ar is phenyl; 0–6 where Ar is naphthyl; and 0–8 where Ar is phenanthryl or anthracenyl;

each $R_1$ and $R_2$ is independently selected from alkyl, aryl, aralkyl, alkaryl or cycloaliphatic radicals, or substituted derivatives thereof wherein substituted derivatives include ethers, amines, amides, sulfonic acids, esters, hydroxyl groups and alkoxy groups;

each $R_3$ and $R_4$ is independently selected from hydrogen and the $R_1$ substituents;

each of the above alkyl groups or moieties is straight or branched chain of 1–20 carbons;

each aryl group contains 6–10 ring carbons;

each cycloaliphatic group contains from 4–8 ring carbons; and each Y is independently selected from the elements P, As, Sb and Bi.

The invention process comprises (1) contacting a biaryl compound having the structural formula:

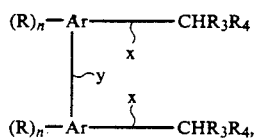

with a proton abstracting agent under conditions suitable to form a biaryl dianion, and thereafter (2) contacting the biaryl dianion with a Group V compound of the formula:

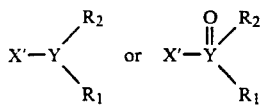

wherein X' is a halogen or a suitable leaving group, and Y, $R_1$ and $R_2$ are as defined above.

It is recognized, of course, that in order to obtain the desired bidentate ligand, the initially formed condensation product will require an additional reduction step when the oxygenated-Group V compound is employed as the source of the P, As, Sb or Bi moiety.

In a particular embodiment of the present invention, the bidentate ligands prepared in accordance with the invention process are compounds of the formula:

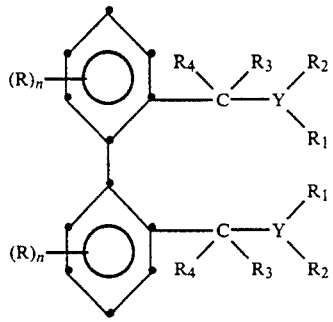

wherein:

n is 0-4;

each R is independently selected from alkyl, alkoxy, aryloxy, aryl, aralkyl, alkaryl, alkoxyalkyl, aryloxyalkyl, cycloaliphatic, halogen, alkanoyl, aroyl, alkanoyloxy, aroyloxy, alkoxycarbonyl, aryloxy carbonyl, cyano, carboxyl, sulfonic acid, or formyl radicals;

each $R_1$ and $R_2$ is independently selected from alkyl, aryl, aralkyl, alkaryl or cycloaliphatic radicals, or substituted derivatives thereof, wherein substituted derivatives include ethers, amines, amides, sulfonic acids, esters, hydroxyl groups and alkoxy groups;

each $R_3$ and $R_4$ is independently selected from hydrogen and the $R_1$ substituents;

each of the above alkyl groups or moieties is straight or branched chain of 1-20 carbons, preferably 1-8 carbons, each aryl group contains 6-10 ring carbons, and each cycloaliphatic group contains from 4-8 ring carbons; and each Y is independently selected from the elements P, As, Sb and Bi, with P being preferred.

In another particular embodiment of the present invention the bidentate ligands prepared in accordance with the invention process are compounds of the general formula:

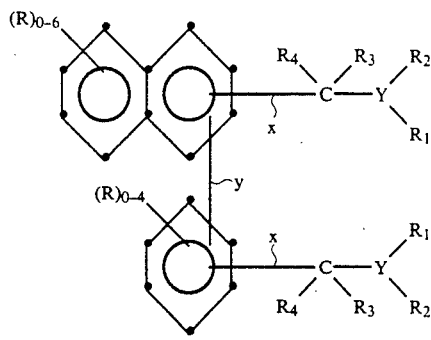

wherein:

the x bonds and the y bonds are attached to adjacent carbon atoms on the ring structures;

each R when present as a substituent is independently selected from alkyl, alkoxy, aryloxy, aryl, aralkyl, alkaryl, alkoxyalkyl, aryloxyalkyl, cycloaliphatic, halogen, alkanoyl, aroyl, alkanoyloxy, aroyloxy, alkoxycarbonyl, aryloxy carbonyl, cyano, carboxyl, sulfonic acid or formyl radicals;

each $R_1$ and $R_2$ is independently selected from alkyl, aryl, aralkyl, alkaryl or cycloaliphatic radicals, or substituted derivatives thereof, wherein substituted derivatives include ethers, amines, amides, sulfonic acids, esters, hydroxyl groups and alkoxy groups;

each $R_3$ and $R_4$ is independently selected from hydrogen and the $R_1$ substituents;

each of the above alkyl groups or moieties is straight or branched chain of 1-20 carbons, preferably 1-8 carbons, each aryl group contains 6-10 ring carbons, and each cycloaliphatic group contains from 4-8 ring carbons; and each Y is independently selected from the elements P, As, Sb and Bi, with P being preferred.

In yet another particular embodiment of the present invention, the bidentate ligands prepared in accordance with the invention process are compounds of the general formula:

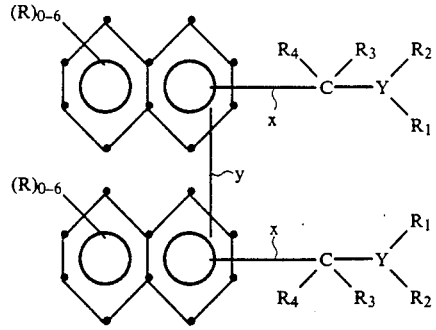

wherein:

the x bonds and the y bonds are attached to adjacent carbon atoms on the ring structure;

each R when present as a substituent is independently selected from alkyl, alkoxy, aryloxy, aryl, aralkyl, alkaryl, alkoxyalkyl, aryloxyalkyl, cycloaliphatic, halogen, alkanoyl, aroyl, alkanoyloxy, aroyloxy, alkoxycarbonyl, aryloxy carbonyl, cyano, carboxyl, sulfonic acid or formyl radicals;

each $R_1$ and $R_2$ is independently selected from alkyl, aryl, aralkyl, alkaryl or cycloaliphatic radicals, or substituted derivatives thereof, wherein substituted derivatives include ethers, amines, amides, sulfonic acids, esters, hydroxyl groups and alkoxy groups;

each $R_3$ and $R_4$ is independently selected from hydrogen and the $R_1$ substituents;

each of the above alkyl groups or moieties is straight or branched chain of 1-20 carbons, preferably 1-8 carbons, each aryl group contains 6-10 ring carbons, and each cycloaliphatic group contains from 4-8 ring carbons; and each Y is independently selected from the elements P, As, Sb and Bi, with P being preferred.

Especially preferred compounds which can be prepared in accordance with the invention process include:
2,2'-bis(diphenylphosphinomethyl)-1,1'-biphenyl (hereinafter, BISBI);
2,2'-bis(dibenzylphosphinomethyl)-1,1'-biphenyl;
2,2'-bis(phenylbenzylphosphinomethyl)-1,1'-biphenyl;
2,2'-bis(diisobutylphosphinomethyl)-1,1'-biphenyl;
2-(diphenylphosphinomethyl)-1-[2-(diphenylphosphinomethyl)phenyl]naphthalene; and
2,2'-bis(diphenylphosphinomethyl)-1,1'-binaphthyl.

The biaryl compounds employed in the practice of the present invention can be prepared by a variety of synthetic routes known by those of skill in the art. For example, a reactant of the formula:

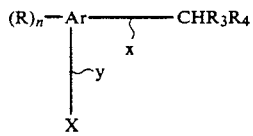

can be subjected to coupling conditions for a time suitable to produce the desired biaryl compound.

One such coupling reaction involves maintaining a redox reaction system comprising a reactant of the formula:

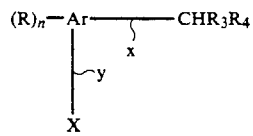

a polar, aprotic solvent, a nickel compound, a triorganophosphorus ligand, and a reducing agent at a temperature suitable for coupling for a time sufficient to form the desired biaryl compound.

Other coupling reactions include the nickel promoted coupling of aryl Grignard reagents; the nickel-phosphine complex catalyzed coupling of aryl Grignard reagents with aryl bromides and iodides; the dehalogenation of aryl bromides and iodides in the presence of highly activated Ni(O) powders; the reaction of aryl iodides with Cu(O) at elevated temperatures (e.g., 200° C.); the palladium-phosphine complex catalyzed coupling of aryl Grignard reagents with aryl halides; and the like.

The presently preferred method for the preparation of bis(alkyl substituted) biaryl compounds employed in the practice of the invention process is the coupling reaction first described above, i.e., the redox reaction system comprising an alkyl-substituted aryl halide, a polar, aprotic solvent, a nickel compound, a triorganophosphorus ligand and a reducing agent.

This presently preferred reductive coupling reaction is generally carried out at a temperature in the range of about 30° C. up to 150° C., preferably between about 50° C. up to about 90° C.

Reaction pressure employed for this reductive coupling is not critical. Typically, this reaction is carried out at atmospheric pressure, although higher and lower pressures can be employed.

The reducing agent metal is generally present with respect to the nickel compound in a molar ratio in the range of about 5/1 up to 1,000/1, preferably in the range of about 10/1 up to 400/1, and most preferably from about 25/1 to about 100/1, although higher or lower ratios may be used. Very low ratios, however, will typically result in incomplete reaction and low yield.

It is also preferred that the ratio of polar, aprotic solvent (in mL) with respect to the reactant (aryl halide, in moles) be in the range of about 100/1 up to 10,000/1, and most preferably in the range of about 200/1 up to 2,000/1. The molar ratio of nickel compound with respect to the reactant (aryl halide) should be in range of about 1/100 up to ½, preferably in the range of about 1/40 up to 1/5, and most preferably in the range of about 1/30 up to 1/10. While higher or lower ratios may be used, there are no practical reasons therefor.

Solvents suitable for use in the practice of this preferred coupling reaction are polar (i.e., high dipole moment), aprotic solvents, such as, for example, dimethylformamide, dimethylacetamide, N-methyl pyrrolidone, N,N-dimethyl benzamide, N-methyl piperidone, benzonitrile, tetramethyl urea, hexamethylphosphoric triamide, and the like.

A wide range of nickel compounds are suitable for use in the practice of the presently preferred coupling reaction, so long as the nickel compounds employed are essentially water-free. The nickel (II) halide salts are a convenient source of nickel as such compounds are readily available in anhydrous form; or hydrated forms of nickel (II) halide salts can be employed, with a dehydration step by such well known techniques as azeotropic distillation being employed to remove the water of hydration. Those of skill in the art recognize that a wide variety of other nickel compounds can be used, e.g., nickel nitrates, sulfates, phosphates, oxides, carbonates, carboxylates, acetylacetonate and the like, as well as Ni(O) complexes such as, for example, bis(1,5-cyclooctadienyl)nickel(O), nickel(O) tetracarbonyl, and the like.

The nickel (II) halides are presently preferred because of their ready availability in anhydrous form, and because the presence of halides in the reaction mixture appears to promote the coupling reaction.

When halide-free nickel compounds are employed, it may be desirable to provide a source of halide to the reaction mixture. A convenient supplemental source of halide is an alkali metal halide, preferably as the sodium or potassium halide. Up to about 200 moles of halide per mole of nickel will impart a beneficial effect on the coupling reaction, with about 10 up to 80 moles of halide per mole of nickel being preferred. In a most preferred embodiment, about 20 up to 50 moles of halide per mole of nickel will be added to the coupling reaction mixture.

A wide range of organophosphorus ligands are useful in this coupling reaction, including triarylphosphines such as triphenylphosphine; alkyl or substituted alkyl diphenylphosphines, such as butyl diphenyphosphine, diphenyl-2-(N-ethylpyrrolidono)-phosphine; alkoxy-substituted diphenyl-alkyl phosphines such as diphenyl- (2-methoxyethoxy ethyl)phosphine and diphenyl-(2-ethoxyethyl)-phosphine; and the like. In addition, bidentate ligands such as 2,2'-bipyridyl, 1,10-phenanthroline, 1,8-naphthyridine ( i.e., 1,8-diazanaphthalene), 2-(dimethylamino)pyridine, and the like, can be employed.

The reducing agent employed in the preferred coupling process will have a sufficient reducing potential to promote the reduction of Ni(II) to Ni(O). Thus, any element with an electromotive force (EMF) more negative than −0.25 V (relative to hydrogen) could be employed. Elements which satisfy this criterion include calcium, zinc, magnesium, manganese, sodium and lithium. Presently preferred elements are zinc, magnesium and manganese.

While the reducing agent employed in the presently preferred coupling process is preferably internal to the reaction system, those of skill in the art recognize that the known external reducing agent, an electrochemical cell, can also be used. In such a system, conventional E.M.F. values for the particular concentrations of the aryl halide reactant to be coupled, nickel compound and electrolyte, e.g., tetrabutylphosphonium bromide, lithium bromide, etc., can be employed. The determinations of such E.M.F., component concentrations, bath size and the like can readily be carried out by those skilled in the art.

A typical useful electrochemical cell is

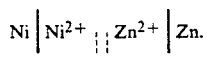

Undivided cells may also be used. In carrying out such an electrochemical reaction in the laboratory, the following parameters are exemplary for coupling 2-halotoluenes (2-HT).

| Bath size | 1.0 L |
| --- | --- |
| Dimethylformamide | 500 mL |
| 2-HT | 0.4 moles |
| NiCl$_2$ | 0.02 moles |
| LiBr | 0.3 N |
| E.M.F. | −1.5 volts (relative to the Saturated Calomel Electrode) |

It is preferred to agitate the bath in known manner and to maintain the electrochemical reaction mixture at a temperature suitable for producing the coupled product. The temperature of the electrochemical reaction mixture is preferably maintained in the range of about 30° C. to 150° C., and most preferably in the range of about 50° C. up to 90° C.

In the reductive coupling reaction, the solvent employed is preferably dimethylformamide or dimethylacetamide, or mixtures thereof; the nickel compound employed is preferably nickel chloride or nickel bromide, or mixtures thereof; the stabilizing ligand is a triorganophosphine; and the reducing metal employed is preferably finely divided, preferably powdered, zinc, magnesium or manganese, or mixtures of two or more thereof.

During the reductive coupling reaction, the concentrations of the various reactant materials and their ratios as set forth above will necessarily change and it is preferred for continuous operations that their concentrations be maintained at least within the specified broad ranges by addition of these reactants to the reaction system as is necessary.

It is also noted with respect to the above stated reaction conditions, that the temperatures employed will be dictated to a degree by the particular reactants employed, and also by the size and design of the equipment. For example, the thermal stability of these materials must be considered and any exotherm monitored to prevent degradation or excessive side reactions. The pressure of the reductive coupling reaction systems need only be ambient, and lower or higher pressures give no significant enhancement to the reaction and typically are not warranted.

In regard to the isolation and work up of the coupled product, the procedure generally involves the following sequence of steps: aqueous quench, filtration, aqueous washes, and distillation. Alternatively, concentration, recrystallization, and the like are acceptable.

The biaryl compound employed in the practice of the present invention is first contacted with a proton abstracting agent under conditions suitable to form a biaryl dianion, which is thereafter contacted with a Group V compound of the formula:

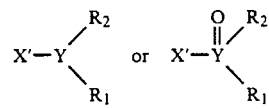

wherein X' is halogen or a suitable leaving group, and wherein Y, R$_1$ and R$_2$ are as previously defined, either as the unprotected moiety, or in a protected and/or latent form, as appropriate, so as to be compatible with the reaction conditions of the ligand forming reaction. Similarly, R, R$_3$ and R$_4$ of the biaryl moiety will be either in the unprotected form or in a protected and/or latent form so as to be compatible with the reaction conditions of the ligand-forming step.

It is recognized, of course, that in order to obtain the desired bidentate ligand, the intially formed condensation product will require an additional reduction step when the oxygenated-Group V compound is employed as the source of the P, As, Sb or Bi moiety.

Proton abstracting agents are typically strong bases which are capable of abstracting relatively labile hydrogens. Exemplary agents have a general structural formula:

wherein R' is hydrogen, C$_1$–C$_{10}$ alkyl, amide (NR'$_2$), and M is selected from the group consisting of Li, Na, K and Cs. Compounds which satisfy this general formula include n-butyl lithium, methyl lithium, sodium amide, t-butyl lithium, potassium t-butoxide, n-butyl lithium/potassium t-butoxide mixture, lithium diisopropylamide, sec-butyl lithium, potassium hydride, sodium hydride, lithium dicyclohexylamide, lithium hexamethyl disilazide, lithium tetramethylpiperidide, and the like, as well as mixtures of any two or more thereof.

Optionally, the proton abstracting agent will further comprise a cation complexing agent which acts to increase the effective basicity (i.e., the ability to abstract a proton) of the base (i.e., proton abstracting agent) employed. The use of such agents is preferred with less active proton abstracting agents and/or to increase the rate of formation of the desired biaryl dianion. Exemplary cation complexing agents include:

diazabicyclo [2.2.2] octane (DABCO),
N,N,N',N'-tetramethyl ethylenediamine (TMEDA),
N,N,N',N'-tetraethyl ethylenediamine (TEEDA),
1,5-diazabicyclo[4.3.0]non-5-ene (DBN),
1,8-diazabicyclo[5.4.0]undec-7-ene (DBU),
N,N,N',N'',N''-pentamethyl diethylenetriamine (PMDT),
crown ethers, e.g., 18-crown-6, 15-crown-5, and 12-crown-4,
and the like, as well as mixtures of any two or more thereof.

When employed, the cation complexing agent can be present in the range of from about 0.5 up to 5 equivalents per equivalent of the proton abstracting agent. Preferably, for most efficient use of reagents, about 2 equivalents of cation complexing agent (i.e., 1 mole of dibasic amine cation complexing agent) will be employed per equivalent of proton abstracting agent. Presently preferred is the combination of n-butyl lithium and TMEDA because of its ready availability, relatively low cost, excellent reactivity and ease of by-product removal from the reaction mixture.

The contacting of biaryl compound with proton abstracting agent can be carried out in a variety of sequences and over a wide range of reaction conditions. The proton abstracting agent and biaryl compound can be combined in any manner known to those of skill in the art, for example, by slow addition of the biaryl compound to a solution of the proton abstracting agent, or by slow addition of the proton abstracting agent to the biaryl compound.

Similarly, when cation complexing agent is also employed for the dianion-forming step, the three reagents can be combined in any order. One preferred means of combining cation complexing agent, proton abstracting agent and biaryl compound is to premix the cation complexing agent with the proton abstracting agent, and then slowly add the biaryl compound to the premixed proton abstracting system. An alternate preferred embodiment entails premixing the biaryl compound with the cation complexing agent, then adding the proton abstracting agent thereto.

Typically, reaction is carried out at a temperature in the range of about 0° up to 100° C., with temperatures in the range of 20° up to 70° C. being preferred. Typically, the rate of addition of the limiting reagent to the reaction mixture is controlled so as to maintain the reaction temperature in the desired range.

Once all of the reagents employed for the dianion-forming step have been combined, it is preferred to maintain the reaction mixture under reaction conditions for a time sufficient to allow the dianion-forming reaction to reach equilibrium. Typically, a time of about 0.1 up to 48 hours is suitable for this purpose, with reaction times in the range of about 0.5 up to 24 hours being preferred. Those of skill in the art recognize that shorter reaction times are required when higher reaction temperatures are used, and vice versa.

Solvents employed for the dianion-forming reaction are those solvents which are non-reactive with the proton abstracting agent, i.e., aprotic solvents such as hydrocarbons (e.g., hexane, heptane, octane, cyclohexane, and the like), ethers (e.g., tetrahydrofuran, glyme, diglyme, anisole, and the like), and the like. Typically, the proton abstracting agent is employed as a solution in a suitable solvent, at a concentration in the range of about 0.2 up to 12.0M; with a preferred concentration in the range of about 1 up to 3M.

The biaryl compound may typically be used with or without solvent. When solvent is used, concentrations of biaryl compound as low as 0.1M in suitable solvent are acceptable, with concentrations of about 0.5M or greater being preferred.

While the quantity of proton abstracting agent employed can vary widely, it is desirable to use at least 0.5 equivalents of proton abstracting agent per mole of biaryl compound up to about 5 equivalents of proton abstracting agent per mole of biaryl compound, for efficient utilization of the valuable biaryl compound. Preferably, there will be employed in the range of about 1.8 up to 2.5 equivalents of the agent per mole of biaryl compound for most efficient utilization of all reagents.

Once formation of the biaryl dianion is substantially complete, it is preferred to purify the dianion to remove reaction by-products and unreacted starting materials which would otherwise tend to reduce the yield of bidentate ligand produced in the subsequent conversion step. The isolation of relatively pure dianion can be accomplished employing techniques well known by those of skill in the art, such as, for example, filtration, centrifugation, decantation, and the like.

In a preferred embodiment, the biaryl dianion is formed using the n-BuLi/TMEDA complex in a hydrocarbon solvent, such as, for example, hexane or heptane. Under such conditions, the dianion complex is a solid and separates from the solvent, and can, therefore, be readily purified by filtration with subsequent washing with a sufficient quantity of solvent (e.g., hexane or heptane) to remove residual impurities from the dianion-forming reaction.

The biaryl dianion is then contacted with a Group V compound of the formula:

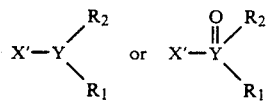

wherein X' is a halogen or a suitable leaving group, e.g., tosylate, mesylate, brosylate, and the like; under conditions suitable to form the desired bidentate ligand.

This contacting is typically carried out in the presence of a diluent such as an aprotic dialkyl ether, e.g., diethyl ether, tetrahydrofuran (THF), and the like, ethylene glycol dialkyl ethers, particularly ethylene glycol dimethyl-, dipropyl-, and dibutyl-ethers; hydrocarbons such as hexane, heptane, cyclohexane, and the like; aromatics having no acidic protons, such as benzene, t-butylbenzene, and the like; or mixtures of any two or more thereof, e.g., THF/hexane; with the presently most preferred diluent being hexane or heptane. The ratio of biaryl dianion to diluent can vary broadly, e.g., 0.01 up to 10 moles of dianion per liter of diluent (mol/L). Preferably, the ratio of dianion to diluent will fall within the range of 0.1 up to 4 mol/L; with ratios in the range of 0.3 up to 2 mol/L being most preferred.

With respect to Group V compound, the concentration of Group V compound can also vary widely, with concentration typically falling in the range of 0.01 up to 10 moles per liter of solvent (mol/L). Preferably, the concentration of Group V compound will fall within the range of 0.5 up to 5 mol/L; and concentrations in the range of about 1 up to 3 mol/L being most preferred.

The reaction is carried out at a temperature in the range of about 0° C. up to 100° C., preferably at about 30°-60° C. Reaction pressure is not critical, and is preferably about one atmosphere.

The biaryl dianion and Group V compound can be contacted in either sequence, i.e., by adding Group V compound to the dianion or vice versa. Reverse addition, i.e., addition of dianion to the Group V compound, is presently preferred because higher yields of the desired bidentate ligand are obtained when this mode of addition is employed.

The molar ratio of the biaryl dianion to the diorgano-Group V halide reactant can vary widely. Ratios of about 1 mole of dianion per 2 moles of diorgano-Group V halide reactant are preferred for efficient utilization of reagents employed; with ratios in the range of 1/1.8-2.5 (moles of dianion per mole of diorgano-Group V halide reactant) being most preferred.

Once the desired bidentate ligand has been prepared, standard purification techniques can be employed to remove by-product salts and organic materials. Such techniques include product crystallization/recrystallization, filtration, extraction, and the like. Those of skill in the art recognize that the supernatant liquid, containing unconverted and partially converted biaryl compound, can be recycled to the dianion-forming step to increase the overall efficiency of feed utilization.

The following non-limiting examples will further illustrate the invention:

EXAMPLES

All operations using or producing organolithium reagents or organophosphines were conducted under an inert atmosphere of nitrogen utilizing deoxygenated solvents. Tetrahydrofuran (THF) was distilled from sodium/benzophenone ketyl under nitrogen.

EXAMPLE 1: The Ni-Zn Promoted Preparation of 2,2'-Dimethyl-1,1'-Biphenyl

To a 2-liter resin kettle equipped with a cooling coil (3 foot by ¼ inch 316 stainless steel), thermometer, heating jacket, Dean-Stark trap, an efficient stirrer, and a condenser was added nickel chloride hexahydrate (35.6 grams, 0.15 mole), triphenylphosphine (120 grams, 0.458 mole), dimethyl-formamide (600 mL) and toluene (200 mL). The mixture was heated to reflux and the water was collected in the Dean-Stark trap and removed. The reflux conditions were maintained for about 1 hour to remove all water from the reaction mixture. At this time, the Dean-Stark trap was drained repeatedly to remove most of the toluene. The catalyst solution was then allowed to cool to ambient temperature and the Dean-Stark trap removed.

Zinc powder (−325 mesh, 260 grams, 3.97 moles) was washed under nitrogen sequentially with 2 percent aqueous HCl (2×200 mL), water (2×200 mL), absolute ethanol (2×100 mL), and finally with diethyl ether (2×150 mL). The powder was dried by passing dry nitrogen through the filter cake. The dry zinc powder and sodium bromide (45 grams) were then added to the resin kettle containing the remainder of the catalyst components whereupon the color of the mixture changed from a deep blue to a reddish brown indicating the presence of Ni(O) species.

2-Chlorotoluene (385 grams, 3 moles) was placed in an addition funnel and attached to the resin kettle. An aliquot of chlorotoluene (50 mL) was added to the kettle and the mixture stirred and heated (steam heat in coil and heating jacket) until the reaction mixture had reached 80° C. The reaction mixture was held at 80° by the addition of water to the steam with the mixing of the two being controlled by a Thermowatch ® temperature controller. In practice, the temperature of the contents of the reaction varied between 78.5° and 81° C. The remainder of the 2-chlorotoluene was added dropwise over a 30-minute period and the reaction mixture held at 80° C. with good stirring for 14 hours. The reaction mixture was then cooled to ambient whereupon the liquid separated into two phases with the excess zinc precipitated in the bottom of the kettle. Heptane (100 mL) was added, the layers mixed, allowed to reseparate, and the top layer was siphoned off into a separatory funnel. The addition of heptane, mixing, and separation was repeated three additional times and the combined heptane layers were then washed with water (2×400 mL), and distilled to give the product. The heptane was removed through a twenty-five tray Oldershaw column at atmospheric pressure (under nitrogen) and the final distillation was done at 25 mm Hg through a ten-bubble cap Snyder column to give:

2-Chlorotoluene (20.15 grams recovered; 5.23 percent of starting charge)

2,2'-dimethyl-1,1'-biphenyl (241.4 grams; 88.4 percent of theory; boiling point 139° to 140° C. at 25 mm Hg)

Overall, the reaction showed 94.7 percent conversion of 2-chloro-toluene with a 93.4 percent selectivity for 2,2'-dimethyl-1,1'-biphenyl.

EXAMPLE 2: The Preparation of 2,2'-Dimethyl-1,1'-Biphenyl Employing Aryl Grignards To a suspension of magnesium turnings (12.15 grams, 0.5 mole) in THF (150 mL) was added 2-chlorotoluene (50.6 grams, 0.40 mole). The mixture was refluxed for 18 hours, cooled to ambient and added dropwise to a solution of 2-chlorotoluene (44.3 grams, 0.35 mole) and bis(triphenylphosphine)-nickel (II) dichloride (2.0 grams) in THF (250 mL). The reaction mixture warmed upon mixing and was heated to reflux for 4 hours after completion of the addition. The reaction mixture was cooled and quenched by the addition of toluene (400 mL) and a saturated ammonium chloride solution (200 mL). The layers were separated and the organic phase was washed sequentially with 10 percent HCl (200 mL), water (3×100 mL), and then stripped under nitrogen to give a thick oil. The oil was distilled under vacuum to give the product as a fraction boiling in the range of 85° to 90° C. at 1 mm Hg. The yield was 43.40 grams (68 percent of theory) of 2,2'-dimethyl-1,1'-biphenyls containing 93 percent of the 2,2'-isomer and 3.5 percent of other isomers.

EXAMPLE 3: Preparation of 2,2'-Bis(diphenylphosphinomethyl)-1,1'-biphenyl

N,N,N',N'-Tetramethylethylenediamine (TMEDA) (14.7 mL, 97.6 mmol) was added via syringe to a 1.6 molar solution of n-butyllithium in hexane (60.7 mL, 97.1 mmol) under nitrogen in a 3-neck, 500-mL, round-bottom flask. 2,2'-Dimethyl-1,1'-biphenyl (8.76 grams, 48.1 mmol) was added and the solution was heated at 65° C. (oil bath) for 1 hour, during which time the dianion separated as a red oil which eventually formed a yellow-orange solid. The mixture was allowed to cool to room temperature and was then vacuum-filtered under nitrogen and the solid was washed with hexane (3×30 mL). 2,2'-Dimethyl-1,1'-biphenyl (3.06 grams)

was recovered from the filtrate, indicating a yield of dianion of 65 percent. Hexane (80 mL) was added to the solid dianion and the resulting slurry was added over about 20 minutes to a solution of chlorodiphenylphosphine (11.1 mL, 61.9 mmol) in hexane (50 mL). The reaction mixture was stirred at room temperature for an additional 15 minutes. Anhydrous ethanol (5 mL) was then added and stirring was continued for about 5 minutes. Water (40 mL) and toluene (60 mL) were then added and the mixture was stirred vigorously. The layers were separated and the organic layer was washed twice with water (50 mL each), then evaporated on a steam bath under a stream of nitrogen. The residual amber oil was dissolved in hot n-propanol (100 mL) and the solution was then allowed to stand overnight at room temperature whereupon the product precipitated as the white solid. The yield of BISBI was 12.82 grams (75 percent based on chlorodiphenylphosphine and unrecovered 2,2'-dimethyl-1,1'-biphenyl).

EXAMPLE 4: Large-Scale Preparation of 2,2'-Bis(diphenylphosphinomethyl)-1,1'-Biphenyl Into a 5-liter, 3-neck flask equipped with a bottom-drain stopcock, and fitted with a thermometer in a thermowell, mechanical stirrer, and Claisen adapter, (which in turn was fitted with an addition funnel and condenser with a nitrogen adapter) were first placed n-BuLi (825 mL of 1.6M, 1.32 moles) and N,N,N',N'-tetramethylethylene diamine (202 mL, 155 grams, 1.34 moles), followed by the addition of 2,2'-dimethyl-1,1'-biphenyl (123 grams, 0.677 moles) to the reaction flask. The mixture exothermed to about 45° C. and was then heated up to 56° to 60° C. for 1 hour. A yellow solid precipitated out of solution during this time. After cooling to 30° C. the thermowell was replaced with a filter stick (glass frit). The mother liquor was removed via the filter stick with a vacuum pump. The remaining yellow dianion was washed with 3×1,000 mL of deoxygenated hexane. Each wash was removed via the filter stick. GC analysis of the mother liquor and washes indicated that 47.2 grams (0.26 moles) of 2,2'-dimethyl-1,1'-biphenyl was recovered. Another 500 mL of hexane was added to the dianion. This slurry was added through the bottom stopcock of the reaction flask to chlorodiphenylphosphine (157 mL, 193 grams, 0.875 moles) in 500 mL of hexane over 30 minutes with stirring. The mixture exothermed to about 60° C. The remaining dianion was washed into the reaction mixture with 3×100 mL of hexane over 15 minutes. After stirring an additional 15 minutes the mixture was quenched with 100 mL of ethanol. Toluene (400 mL) was then added and the mixture was washed with water (4×1,000 mL). Solvent was removed from the reaction mixture by distillation at a pot temperature of up to 150° C. The crude product was recrystallized from 1,400 mL of n-propanol. BISBI (160.6 grams, 70 percent yield on unrecovered bitolyl, 67 percent yield on chlorodiphenylphosphine) was obtained following vacuum filtration, washing with 3×300 mL of n-propanol, and drying in a vacuum desiccator (1 mm Hg, 3 hours).

EXAMPLE 5: Preparation of 2,2'-Bis(diphenylphosphinomethyl)-1,1'-Biphenyl Using Tetrahydrofuran as Solvent for Dianion N,N,N',N'-Tetramethylethylenediamine (TMEDA) (14.7 mL, 97.6 mmol) was added via syringe to a 1.6 molar solution of n-butyllithium in hexane (60.7 mL, 97.1 mmol) under nitrogen in a 3-neck, 500-mL, round-bottom flask. 2,2'-Dimethyl-1,1'-biphenyl (8.76 grams, 48.1 mmol) was added and the solution was heated at 65° C. (oil bath) for 1 hour, during which time the dianion separated as a red oil which eventually formed a yellow-orange solid. The mixture was allowed to cool to room temperature and was then vacuum-filtered under nitrogen and the solid washed with hexane (3×30 mL). Hexane (20 mL) was added to the yellow solid and the slurry cooled to 0° to 5° C. in an ice bath. Cold (5° C.) tetrahydrofuran (THF, 80 mL) was added to the dianion/hexane slurry and the mixture stirred in an ice bath for about 5 minutes to allow all the solid to dissolve. The cold dark red-brown solution was added over 15 minutes to a solution of ClPPh$_2$ (12.0 mL, 66.8 mmol) in hexane (50 mL), causing an exotherm to about 45° C. The reaction mixture was stirred without further heating for an additional 15 minutes. Anhydrous ethanol (5 mL) was then added and stirring continued for about 5 minutes. Water (40 mL) and toluene (60 mL) were then added and the mixture stirred vigorously. The layers were separated and the organic layer was washed twice with water (50 mL each), then evaporated on a steam bath under a stream of nitrogen. The residual amber oil was dissolved in hot n-propanol (140 mL) and the solution allowed to stand overnight at room temperature whereupon the product precipitated, giving 7.50 grams of BISBI as a white solid. A second crop of 1.07 grams was isolated by concentration of the filtrate. The total yield of BISBI was 8.57 grams (47 percent based on ClPPh$_2$ and unrecovered 2,2'-dimethyl-1,1'-biphenyl).

EXAMPLE 6: Preparation of 2,2'-Bis(diphenylphosphinomethyl)-1,1'-biphenyl Using Modified Procedures The following experiments were performed to prepare BISBI using modifications of the method shown above for Examples 3 and 4. Each of these experiments was run using the following general procedures for preparation of the dianion and reaction with ClPPh$_2$. 2,2'-Bitolyl (8.76 grams, 48.1 mmol), TMEDA (14.7 mL, 97.6 mmol) and hexane (30 mL) were placed in a 3-neck, 500-mL, round-bottom flask fitted with a magnetic stirring bar, condenser, addition funnel and nitrogen gas inlet. A solution of n-BuLi in hexane (1.6 molar, 60.7 mL, 97.1 mmol) was added from the addition funnel to the stirring solution over about 20 minutes. The reaction mixture was stirred at room temperature for 15 to 30 minutes and then was heated in an oil bath at 60° to 65° C. for 2 hours. After cooling to room temperature, the yellow solid was filtered under nitrogen and washed with hexane (4×25 mL). The red filtrate was quenched with ispropanol and analyzed by gas chromatography (using biphenyl as an internal standard) to determine the amount of recovered bitolyl. Hexane (80 mL) was added to the solid yellow dianion to form the dianion/hexane slurry. The slurry was added over 10 to 15 minutes to a solution of ClPPh$_2$ (11.1 mL, 61.9 mmol) in hexane (50 mL) resulting in an exotherm to about 45° C. Residual slurry was rinsed into the reaction mixture with additional hexane (20 mL). The reaction mixture was then allowed to stir for an additional 15 to 30 minutes, resulting in a light yellow solution containing white solid. Individual reactions were worked up and the products were isolated by Methods A to F as described in the following procedures. The yields obtained in these reactions are shown in Table I.

1. Method A—Ethanol (7 mL) was added to the reaction mixture, which was then stirred for about 5 minutes. Water (60 mL) and toluene (60 mL) were added and the mixture was stirred vigorously during which time all solids dissolved. The layers were separated and the organic layer was then washed with water (2×50 mL). The organic solution was evaporated on a steam bath under a stream of nitrogen to give the crude product as an amber oil. The product was recrystallized from n-propanol (100 mL) to give BISBI as a white solid.

2. Method B—n-Propanol (7 mL) was added to the reaction mixture, which was stirred for about 15 minutes and then allowed to stand overnight at room temperature, during which time additional solid precipitated. The solid was filtered under nitrogen and washed with methanol (3×50 mL) to give BISBI.

3. Method C—n-Propanol (7 mL) was added to the reaction mixture, which was stirred for about 15 minutes and was then heated to 60° C. Water (30 mL) was added, causing all solids to dissolve. The mixture was stirred for 5 minutes and the aqueous layer was then removed by cannula. The hot water wash was repeated twice (30 mL each) and the organic layer was then allowed to cool to room temperature and stand overnight. The precipitated BISBI was then isolated by filtration and washed with n-propanol (3×50 mL).

4. Method D—Methanol (50 mL) was added to the reaction mixture and stirred 30 minutes at room temperature, during which time additional solid precipitate formed. The reaction mixture was then allowed to stand overnight at room temperature. The solid was filtered under nitrogen and was then washed with methanol (2×50 mL) to give BISBI.

5. Method E—The reaction mixture was heated to 60° C. and then methanol (30 mL) was added, causing all solids to dissolve, and stirred for 10 minutes at 50° to 55° C. The lower methanol layer was removed by cannula. The hot methanol wash (30 mL) was repeated once, then additional methanol (50 mL) was added resulting in a pale yellow homogeneous layer at 50° C. The solution was allowed to cool with stirring. After about 15 minutes, at about 40° C., BISBI began to precipitate as a white solid. The mixture was allowed to stand overnight at room temperature and the product was isolated by filtration under nitrogen and washed with methanol (2×50 mL).

6. Method F—n-Propanol (7 mL) was added to the reaction mixture, which was then heated to 60° C. Water (30 mL) was added to the hot mixture, causing all solid material to dissolve, and the mixture was stirred for 5 minutes. The aqueous layer was removed by cannula. The hot aqueous wash was repeated twice (30 mL water each). n-Propanol (50 mL) was then added to the hot solution and allowed to cool while stirring. At about 40° C. BISBI began to precipitate as a white solid. The mixture was allowed to cool overnight at room temperature. BISBI was then isolated by filtration under nitrogen and washed with n-propanol (3×50 mL).

7. Method G—After the reaction mixture was heated to 60° C., methanol (50 mL) was added. The pale yellow mixture was heated at about 55° C. for 30 minutes, then stirred for an additional 30 minutes while allowing to cool. The product began to precipitate as a white solid at about 40° C. After standing overnight at room temperature, BISBI was isolated by filtration under nitrogen and washed with methanol (3×50 mL).

TABLE I

YIELD OF BISBI USING VARIOUS WORKUP PROCEDURES

| Method | Yield of % Dianion by GC | BISBI Weight, Grams | % Yield BISBI ClPPh$_2$* | Bitolyl** |
|---|---|---|---|---|
| A | 54 | 9.67 | 56 | 68 |
| B | 56 | 9.49 | 55 | 64 |
| C | 56 | 9.23 | 54 | 62 |
| D | 57 | 11.39 | 66 | 75 |
| E | 58 | 9.57 | 56 | 63 |
| F | 55 | 10.00 | 58 | 69 |
| G | 54 | 9.41 | 55 | 66 |

*Yield based on ClPPh$_2$.
**Yield based on unrecovered 2,2'-dimethyl-1,1'-biphenyl.

These results demonstrate that bidentate ligand product workup can be carried out in a variety of ways, with little effect on the product yield or purity.

EXAMPLE 7: Large-Scale Preparation of 2,2'-Bis(diphenylphosphinomethyl)-1,1'-biphenyl With Modified Workup Procedure 2,2'-Dimethyl-1,1'-biphenyl (117 grams, 0.64 mol), TMEDA (196 mL, 1.30 mol) and hexane (300 mL) were placed in a 3-neck, 5-L, round-bottom flask fitted with a mechanical stirrer, condenser, addition funnel, nitrogen gas inlet, and thermowell. A solution of n-BuLi in hexane (1.6 molar, 800 mL, 1.28 mol) was added from the addition funnel to the stirring solution over about 30 minutes, causing an exotherm to 38° C. Additional hexane (100 mL) was used to rinse the residue from the addition funnel into the reaction pot. The reaction mixture was stirred at room temperature for 30 minutes, causing formation of the dianion as a yellow solid to begin, and then was heated to 58° to 60° C. for 2 hours. After cooling to room temperature, the yellow solid was filtered under nitrogen, using a filter stick (glass frit) attached through a trap to a vacuum pump. The solid dianion was then washed with hexane (3×1,000 mL and then 1×500 mL). The red filtrate was quenched with isopropanol and analyzed by gas chromatography (using biphenyl as internal standard), indicating a yield of 57 percent of dianion. Hexane (1,000 mL) was added to the solid yellow dianion to form the dianion/hexane slurry. The slurry was added over 30 minutes to a solution of ClPPh$_2$ (150 mL, 0.84 mol) in hexane (650 mL) resulting in an exotherm to about 48° C. Residual slurry was rinsed into the reaction mixture with additional hexane (3×100 mL). The reaction mixture was then allowed to stir for an additional 30 minutes, resulting in a light yellow solution containing white solid. n-Propanol (100 mL) was added to the reaction mixture, which was stirred for about 15 minutes and then allowed to stand overnight at room temperature, during which time additional solid precipitated. The solid was filtered under nitrogen, via the filter stick, and washed with methanol (2×1,000 mL). Additional methanol (1,000 mL) was added and the mixture was heated to 50° C. for 15 minutes, then cooled to room temperature and filtered. The solid was washed again with methanol (2×1,000 mL), transferred in methanol (1,000 mL) to a glass-frit filter funnel in a nitrogen-filled glove bag, filtered and washed with methanol (2×500 mL). The solid was then dried in a vacuum desiccator (5 mm Hg, 2 hours) to give 130.57 grams of BISBI (57 percent based on ClPPh$_2$, 65 percent based on unrecovered 2,2'-dimethyl-1,1'-biphenyl).

An additional 6.00 grams was recovered by concentration of the methanol filtrates for a total yield of 136.57 grams (60 percent based on ClPPh$_2$, 68 percent based on unrecovered 2,2'-dimethyl-1,1'-biphenyl).

EXAMPLE 8: Preparation of 2,2'-Bis(diphenylphosphinomethyl)-1,1'-biphenyl Using Mineral Spirits and Heptane as Solvents This experiment was run using the same procedures as shown above for workup Method F, except that the n-BuLi used was a 1.6 molar solution (15 weight percent) in mineral spirits, and heptane was employed to form the dianion slurry and as the solvent for ClPPh$_2$. The yield of dianion was 62 percent by GC and the yield of isolated BISBI was 8.97 grams (52 percent based on ClPPh$_2$, 55 percent based on unrecovered 2,2'dimethyl-1,1'-biphenyl).

The invention has been described in detail with particular reference to preferred embodiments thereof, but it will be understood that variations and modifications can be effected within the spirit and scope of the invention.

I claim:

1. A process for preparing a bidentate ligand of the formula:

$$(R)_n-Ar\underset{x}{\overset{}{\rule{1cm}{0.5pt}}}\underset{}{\overset{R_4\ R_3}{C}}\underset{R_1}{\overset{R_2}{Y}}$$
$$\Big|_{-y}$$
$$(R)_n-Ar\underset{x}{\overset{}{\rule{1cm}{0.5pt}}}\underset{R_4\ R_3}{\overset{}{C}}\underset{R_2}{\overset{R_1}{Y}}$$

wherein:
each Ar is independently selected from aromatic ring compounds having 6 up to 14 carbon atoms;
the x bonds and the y bonds are attached to adjacent carbon atoms on the ring structures;
each R, when present as a substituent, is independently selected from alkyl, alkoxy, aryloxy, aryl, aralkyl, alkaryl, alkoxyalkyl, aryloxy alkyl, cycloaliphatic, halogen, alkanoyl, aroyl, alkanoyloxy, aroyloxy, alkoxycarbonyl, aryloxy carbonyl, carboxyl, sulfonic acid, cyano or formyl radicals;
n is a whole number in the range of 0-4 where Ar is phenyl; 0-6 where Ar is naphthyl; and 0-8 where Ar is phenanthryl or anthracenyl;
each R$_1$ and R$_2$ is independently selected from alkyl, aryl, aralkyl, alkaryl or cycloaliphatic radicals, or substituted derivatives thereof; wherein substituted derivatives include ethers, amines, amides, sulfonic acids, esters, hydroxyl groups and alkoxy groups;
each R$_3$ and R$_4$ is independently selected from hydrogen and the R$_1$ substituents;
each of the above alkyl groups or moieties is straight or branched chain of 1-20 carbons;
each aryl group or moiety contains 6-10 ring carbons;
each cycloaliphatic group contains from 4-8 ring carbons; and
each Y is independently selected from the elements P, As, Sb and Bi;
said process comprising:
(1) contacting a biaryl compound having the structure:

$$(R)_n-Ar\underset{x}{\overset{}{\rule{1cm}{0.5pt}}}CHR_3R_4$$
$$\Big|_{-y}$$
$$(R)_n-Ar\underset{x}{\overset{}{\rule{1cm}{0.5pt}}}CHR_3R_4$$

with a proton abstracting agent under conditions suitable to form a biaryl dianion, which is then
(2) contacted with a Group V compound of the formula:

$$X'-Y\underset{R_1}{\overset{R_2}{\diagup}}$$

where X' is halogen or a suitable leaving group.

2. The process of claim 1 wherein said biaryl compound is prepared by maintaining a redox reaction system comprising
(a) a reactant of the formula:

$$(R)_n-Ar\underset{x}{\overset{}{\rule{1cm}{0.5pt}}}CHR_3R_4$$
$$\Big|_{-y}$$
$$X$$

(b) a polar, aprotic solvent,
(c) a nickel compound,
(d) a coordinating ligand, and
(e) a reducing agent, at a temperature and for a time sufficient to form said biaryl compound.

3. The process of claim 2 wherein the reducing agent is selected from finely divided Zn°, Mg° or Mn° and is present with respect to the nickel compound in a molar ratio of reducing agent to nickel compound in the range of about 5/1 up to 1000/1.

4. The process of claim 2 wherein said redox system is maintained at a temperature in the range of about 30° C. up to 150° C.

5. The process of claim 2 wherein said redox system is maintained at a temperature in the range of about 50° C. up to 90° C.

6. The process of claim 2 wherein said coordinating ligand is selected from the group consisting of:
triphenylphosphine,
n-butyldiphenylphosphine,
diphenyl-2-(N-ethylpyrrolidono)phosphine,
diphenyl-(2-methoxyethoxy ethyl)phosphine,
diphenyl-(2-ethoxyethyl)phosphine,
as well as mixtures of any two or more thereof.

7. The process of claim 1 wherein said biaryl compound is prepared by the nickel-promoted coupling of aryl Grignard reagents having the structural formula:

$$(R)_n-Ar\underset{x}{\overset{}{\rule{1cm}{0.5pt}}}CHR_3R_4.$$
$$\Big|_{-y}$$
$$MgX$$

8. The process of claim 1 wherein said biaryl compound is prepared by the nickel-phosphine complex catalyzed coupling of aryl Grignard reagents having the structure:

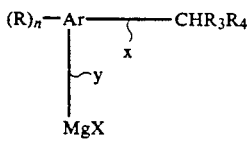

with aryl bromides or iodides having the structure:

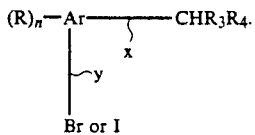

9. The process of claim 1 wherein said biaryl compound is prepared by the Ni(O) promoted dehalogenation of aryl bromides or iodides having the structure:

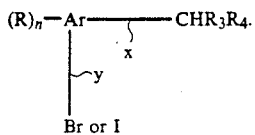

10. The process of claim 1 wherein said biaryl compound is prepared by the high temperature Cu(O) promoted coupling of aryl iodides having the structure:

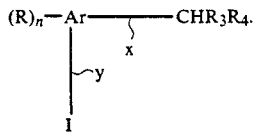

11. The process of claim 1 wherein said biaryl compound is prepared by the Pd-phosphine promoted coupling of aryl Grignard reagents having the structure:

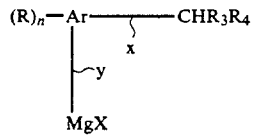

with aryl halides having the structure:

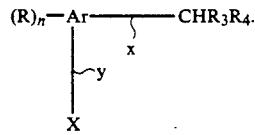

12. The process of claim 1 wherein said proton abstracting agent is an alkali metal compound of the formula:

R'-M wherein R' is H, a $C_1$–$C_{10}$ alkyl or amide ($NR'_2$) moiety, and M is selected from the group consisting of Li, Na, K and Cs.

13. The process of claim 12, wherein said proton abstracting agent further comprises a cation complexing agent.

14. The process of claim 12 wherein said proton abstracting agent is selected from the group consisting of n-butyl lithium, sodium amide, t-butyl lithium, potassium t-butoxide, n-butyl lithium/potassium t-butoxide mixture, lithium diisopropylamide, sec-butyl lithium, potassium hydride, sodium hydride, lithium dicyclohexylamide, lithium hexamethyl disilazide, and lithium tetramethylpiperidide.

15. The process of claim 13 wherein said cation complexing agent is selected from the group consisting of:
diazabicyclo[2.2.2]octane (DABCO),
N,N,N',N'-tetramethyl ethylenediamine (TMEDA),
N,N,N',N'-tetraethyl ethylenediamine (TEEDA),
1,5-diazabicyclo[4.3.0]non-5-ene (DBN),
1,8-diazabicyclo[5.4.0]undec-7-ene (DBU),
N,N,N',N'',N''-pentamethyl diethylenetriamine (PMDT),
crown ethers selected from the group consisting of 18-crown-6, 15-crown-5 and 12-crown-4, and mixtures of any two or more thereof.

16. The process of claim 1 wherein the contacting of said biaryl compound with a proton abstracting agent is carried out at a temperature in the range of about 0° to 100° C. for a time sufficient for the dianion-forming reaction to reach equilibrium.

17. The process of claim 16 wherein unreacted biaryl compound is recycled to the dianion-forming step.

18. The process of claim 13 wherein about 0.5 up to 5 equivalents of said cation complexing agent are employed per mole of said proton abstracting agent.

19. The process of claim 18 wherein about 0.5 up to 5 equivalents of said proton abstracting agent are employed per mole of said biaryl compound.

20. The process of claim 1 wherein said biaryl dianion in a $C_6$–$C_8$ hydrocarbon solvent is added to the Group V compound in a $C_6$–$C_8$ hydrocarbon solvent at a molar ratio in the range of 1/1.8–2.5 at a rate sufficient to maintain the reaction temperature in the range of about 30° up to 60° C.

21. The process of claim 1 wherein said Group V compound is added to said biaryl dianion in a $C_6$–$C_8$ hydrocarbon solvent at a molar ratio in the range of 1.8–2.5/1 at a rate sufficient to maintain the reaction temperature in the range of about 30° up to 60° C.

22. The process of claim 1 wherein the temperature of the reaction medium during the contacting of Group V compound with biaryl dianion is maintained in the range of about −30° up to 100° C.

23. The process of claim 13 wherein said proton abstracting agent is a combination of n-butyl lithium and TMEDA.

24. The process of claim 1 wherein X' is chlorine, $R_3$ and $R_4$ are H, Ar is phenyl, n is zero, and each $R_1$ and $R_2$ is independently selected from phenyl, benzyl, and alkyl radical having 1–6 carbon atoms.

25. The process of claim 24 wherein each $R_1$ and $R_2$ is phenyl.

26. The process of claim 2 wherein the molar ratio of reducing agent to nickel compound falls within the range of about 10/1 up to 400/1, and the molar ratio of the reactant to the nickel compound falls in the range of about 2/1 up to 100/1.

* * * * *